US008568789B2

(12) United States Patent
Kurohashi et al.

(10) Patent No.: US 8,568,789 B2
(45) Date of Patent: Oct. 29, 2013

(54) DRIED PRODUCT AND A PROCESS FOR MANUFACTURING THE PRODUCT

(75) Inventors: Masaharu Kurohashi, Ono (JP); Yoji Shibayama, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/365,048

(22) Filed: Feb. 2, 2012

(65) Prior Publication Data

US 2012/0135083 A1 May 31, 2012

Related U.S. Application Data

(63) Continuation of application No. 11/286,644, filed on Nov. 25, 2005, now abandoned.

(30) Foreign Application Priority Data

| Dec. 1, 2004 | (JP) | 2004-348904 |
| Apr. 28, 2005 | (JP) | 2005-132070 |
| Jun. 17, 2005 | (JP) | 2005-177334 |
| Oct. 13, 2005 | (JP) | 2005-298472 |

(51) Int. Cl.
*A61K 35/12* (2006.01)
*A61K 35/36* (2006.01)

(52) U.S. Cl.
USPC .......................................... 424/520; 424/574

(58) Field of Classification Search
None
See application file for complete search history.

(56) References Cited

U.S. PATENT DOCUMENTS

| 3,957,523 | A | * | 5/1976 | Ohno et al. ............... 106/162.71 |
| 4,145,415 | A | | 3/1979 | Sato |
| 4,640,361 | A | | 2/1987 | Smith et al. |
| 4,863,518 | A | | 9/1989 | Blount |
| 4,985,254 | A | | 1/1991 | Konishi et al. |
| 4,985,354 | A | | 1/1991 | Toyomaki et al. |
| 4,996,988 | A | | 3/1991 | Ohhara et al. |
| 5,013,558 | A | | 5/1991 | Konishi |
| 5,057,324 | A | | 10/1991 | Shibayama et al. |
| 5,534,509 | A | | 7/1996 | Konishi et al. |
| 5,560,935 | A | * | 10/1996 | Konishi et al. ................. 424/520 |
| 5,576,025 | A | | 11/1996 | Akiyama et al. |
| 5,658,896 | A | | 8/1997 | Konishi et al. |
| 5,807,951 | A | | 9/1998 | Konishi et al. |
| 5,977,109 | A | | 11/1999 | Nakakura et al. |
| 6,051,238 | A | | 4/2000 | Volkin et al. |
| 6,051,613 | A | | 4/2000 | Ohno et al. |
| 6,165,515 | A | * | 12/2000 | Matsuyama et al. .......... 424/520 |
| 6,290,967 | B1 | | 9/2001 | Volkin et al. |
| 6,306,345 | B1 | * | 10/2001 | Bronshtein et al. ............. 422/41 |
| 6,365,192 | B1 | | 4/2002 | Konishi |
| 6,541,041 | B1 | | 4/2003 | Konishi |
| 6,576,241 | B2 | | 6/2003 | Konishi |
| 6,726,932 | B2 | | 4/2004 | Konishi |
| 6,774,104 | B1 | | 8/2004 | Sawai et al. |
| 6,913,900 | B2 | | 7/2005 | Kaplan et al. |
| 7,060,308 | B2 | * | 6/2006 | Rajendran et al. ............. 424/725 |
| 8,293,280 | B2 | | 10/2012 | Ansari et al. |
| 2004/0157769 | A1 | | 8/2004 | Sawai et al. |
| 2006/0051375 | A1 | | 3/2006 | Cheung |
| 2006/0134646 | A1 | | 6/2006 | Ansari et al. |

FOREIGN PATENT DOCUMENTS

| EP | 0300973 | 1/1989 |
| EP | 0315591 | 5/1989 |
| EP | 0341209 | 11/1989 |
| EP | 0348353 | * 12/1989 |
| EP | 0621038 | 10/1994 |
| EP | 0645142 | 3/1995 |
| EP | 0733636 | 9/1996 |
| EP | 0919238 | 6/1999 |
| EP | 0953352 | 11/1999 |
| EP | 1557171 | 7/2005 |
| FR | 2610523 | 8/1988 |
| FR | 2617488 | 7/1992 |
| FR | 2720068 | 11/1995 |
| GB | 697351 | 9/1953 |
| JP | 53-101515 | 9/1978 |
| JP | 55087724 | 7/1980 |
| JP | 57-77697 | 5/1982 |
| JP | 57-183720 | 11/1982 |
| JP | 58-35117 | 3/1983 |
| JP | 58-121217 | 7/1983 |
| JP | 62-145022 | 6/1987 |
| JP | 1319422 | 2/1989 |
| JP | 1265028 | 10/1989 |
| JP | 2028119 | 1/1990 |
| JP | 2-73020 | 3/1990 |
| JP | 2-000707 | 5/1990 |

(Continued)

OTHER PUBLICATIONS

Machine Translation for JP 2000-086528, Ishida Hiroyuki, Mar. 2000, pp. 1-9.*
U.S. Appl. Nol. 13/538,408, filed Sep. 7, 2012, Tamaki.
Database WPI, Section Ch, Week 9411, Derwent, XP002113091 & RU 2003338 C, Nov. 30, 1993, abstract.
Database WPI, Section CH, Week 9624, Derwent, XP002113090 & CN 1 096 180, Dec. 14, 1994, abstract.
De Reuck J., et al., "A double-blind study of neurotropin in patients with acute ischemic stroke," ACTA Neutrologica Scandinavica vol. 89, No. 5, 1994, pp. 329-335, XP002109696.
Derwert abstract of SU 1933171 A3 (1993).
"Drugs in Japan, Ethical Drugs," Yakugyo Jiho Co., Ltd., 1994, p. 1434.
Gabriellan, Cerebrovascular Injuries Induced by Activation of Platelets and Leukocytes In vivo and Their Correction by Neurotropin, Japan J. Pharmacol., 60:51-54, 1992.

(Continued)

Primary Examiner — Laura Schuberg
(74) Attorney, Agent, or Firm — Greenblum & Bernstein, P.L.C.

(57) ABSTRACT

A dried product of an extract from inflammatory rabbit skin inoculated with vaccinia virus having an inhibitory activity for the production of a kallikrein-like substance is produced by admixing the extract with a saccharide, sugar alcohol or ascorbic acid before reaching dryness, and then drying the admixture to a solid form such as granules. The dried product may be employed to produce a solid preparation for oral administration, such as tablets, having an inhibitory activity for the production of a kallikrein-like substance.

17 Claims, No Drawings

(56) References Cited

FOREIGN PATENT DOCUMENTS

| | | |
|---|---|---|
| JP | 6-122630 | 6/1994 |
| JP | 7-033666 | 3/1995 |
| JP | 7097336 | 3/1995 |
| JP | 8291077 | 11/1996 |
| JP | 2594222 | 12/1996 |
| JP | 10194978 | 7/1998 |
| JP | 11139977 | 5/1999 |
| JP | 2000-016942 | 1/2000 |
| JP | 2000-086528 * | 3/2000 |
| JP | 2000-336034 | 12/2000 |
| JP | 11080005 | 12/2000 |
| JP | 2003-095955 | 3/2003 |
| JP | 2004-300146 | 10/2004 |
| WO | 2004-039383 | 5/2004 |
| WO | 2004-060381 | 7/2004 |
| WO | 2006-065947 | 6/2006 |

OTHER PUBLICATIONS

Habib et al., "Difference spectrophotometric estimation of santonin", JAssoc Off Anal Chem, Sep.-Oct. 1984, 67(5):939-41.

Lin et al., "The anti-flammatory effects of Chinese crude drug prescriptions on experimental arthritis," Am J. Chin Med, 1995, 23(2): 145-52.

Paslawska et al., "Studies on the Optimum Conditions of Extraction of Silicon Species from Plants With Water", Planta Medica, vol. 29, No. 1, 1976, pp. 72-79, & XP002113087.

Patent Abstracts of Japan, "Antiviral Agent", vol. 017, No. 225 (C-1055), May 10, 1993 & JP 04360838.

Piekos et al., "Studies on the Optimum Conditions of Extraction of Silicon Species from Plants With Eater", Planta Medica, vol. 27, 1975, pp. 145-150, XP002113088.

Section CH, Week 9645, Derwent Publication Ltd., Class B04, AN 96-450925 XP002109698 & JP 08 225452 A, Sep. 3, 1996, abstract.

Shimizu et al., "Electrophysiological Study of Neurotropin-Induced Responses in Guinea Pig Hypothalamic-Neurons", Br. Res. Bull., Dec. 1992, 29(6): 767-72.

Sprumont et al., "Morphometrical Quantification of Brain Edema Related to Experimental Multiple Micro-Infarcts in Mice: Assessment of Neurotropin Effect, " Meth Find Exp Clin Pharmacol 1993, 15(3): 169-177, XP002109697.

Steranka et al."Bradykinin as a pain mediator: receptors are localized to sensory neurons, and antagonists have analgesic actions", Proc Nati Acad Sci USA., May 1988, 85(9): 3245-9.

Takeoka, Y. et al., "Influence of Neurotropin on Thymic Microenvironmental Abnormalities of NZB Mice," Int. J. Immunotherapy, XI(2), pp. 49-56 (1995).

Tanaka et al., Int. Clin. Psychopharm., 3(3): 239-44, Medline Abst. No. 91079456 (Jul. 1988).

Tomomaki et al., "Study on the in vitro Assay Method in Evaluating the Inhibiting Effect of various Drugs on the Production of Plasma Kallikrein-Like Activity", Kiso to Rinsho (The Clinical Report), vol. 20, No. 17, 8889-8895 (1986).

Wang et al., Mushroom Biology and Mushroom Products, Proc. Int. Conf. $2^{nd}$, Editor: Royse Daniel J. Publisher: Penn State University, College of Agricultural Sciences, University Park, PA, 1996, pp. 205-208.

Xu et al., "Immunological mechanisms of antitumor activity of some kinds of crude drugs on tumor necrosis factor production", Int J Immunopharmacol, 1989, 11(6): 607-13.

Izutsu, "Stabilization of Protein Structure during Freeze-drying", National Institute of Health Sciences, 2004, pp. 49-52.

Izutsu, "Stabilization of Protein Structure during Freeze-drying", National Institute of Health Sciences, 2003, No. 1, pp. 47-53.

Shirai, "Elucidation of the effect and stabilization mechanism of sugar on freeze concentration and drying", Annual report, Iijima Memorial Foundation for Promotion of Food science and Technology, 1994: 160-163, 1996.

Egawa, "Effect of Sugar on Stabilization of Formulations", Cryobiology and Cryotechnology, vol. 47, No. pp. 46-51, 2001.

* cited by examiner

DRIED PRODUCT AND A PROCESS FOR MANUFACTURING THE PRODUCT

RELATED APPLICATIONS

The present application is a continuation of U.S. patent application Ser. No. 11/286,644 filed Nov. 25, 2005, which claims priority to Japanese Application Nos. 298,472/2005, filed Oct. 13, 2005; 177,334/2005, filed Jun. 17, 2005; 132, 070/2005 filed Apr. 28, 2005; and 348,904/2004, filed Dec. 1, 2004, all of which are hereby incorporated herein by reference in their entirety.

FIELD OF THE INVENTION

The present invention relates to a dried product of an extract from inflammatory rabbit skin inoculated with vaccinia virus and also to a process for manufacturing said dried product.

BACKGROUND OF THE INVENTION

An extract from inflammatory rabbit skin inoculated with vaccinia virus (hereinafter, it may be mentioned as "the present extract") contains a non-protein active substance which is extracted and separated from the inflamed skin tissue of rabbit inoculated with vaccinia virus.

As mentioned in pages 2499 to 2501 of "List of Japanese Ethical Drugs" (2004 (27th Edition), edited by the Japan Pharmaceutical Information Center, published by K. K. Jiho), a pharmaceutical preparation of an extract from inflammatory rabbit skin inoculated with vaccinia virus (product name: Neurotropin) which is a pharmaceutical containing the present extract as an effective ingredient is a very unique preparation. Namely, broad indications such as low back pain, neck-shoulder-arm syndromes, periarthritis scapulohumeralis, osteoarthritis, symptomatic neuralgia, itching accompanied with skin disorders (such as eczema, dermatitis and urticaria), allergic rhinitis, sequelae of subacute myelo-optico-neuropathy (such as coldness, pain and paresthesia/dysesthesia) and post-herpetic neuralgia have been allowed and subcutaneous, intramuscular and intravenous injections and tablets thereof have been approved for manufacture as ethical drugs and placed into the market.

The present extract is derived from a living body and no single effective ingredient has been identified. Accordingly, quantification of the effective ingredient has been carried out by testing its biological activity (titer). More specifically, a biological test method where an analgesic coefficient is determined using SART stress (repeated cold load) mice in which pain threshold lowers from normal animals has been used (*Nippon Yakurigaku Zasshi*, vol. 72, no. 5, pages 573-584, 1974). Thus, an analgesic coefficient is determined by conducting an analgesic test in accordance with a modified Randall-Selitto method using SART mice and a neurotropin unit (NU) is stipulated by an $ED_{50}$ value calculated from an analgesic coefficient for a standard product. A Neurotropin injection contains 1.2 units per 1 mL in terms of a neurotropin unit and Neurotropin tablets contain 4.0 neurotropin units per tablet.

With regard to the present extract, in addition to the aforementioned quantification of analgesic activity, a biological test method measuring an inhibitory activity for the production of a kallikrein-like substance (hereinafter, it may be mentioned as KPI activity) should be carried out in Japan, etc. where pharmaceutical preparations containing the present extract as an effective ingredient have been sold. By confirming that a product has a regulated level or more KPI activity, the quality and the efficacy as a pharmaceutical agent are strictly guaranteed.

Kallikrein is a proteinase which is widely present in plasma and tissues of various animals and an enzyme system called a kallikrein-kinin system has been known. In plasma, inactive pre-kallikrein is converted to active plasma kallikrein via activation of blood coagulation factor XII and the resulting plasma kallikrein acts on high-molecular weight kininogen in plasma whereupon bradykinin which is a chemical mediator of nonapeptide is liberated. Bradykinin has various actions such as a strong generation of pain by stimulation of sensory nerves, hypotension by dilation of blood vessels and expression of edema by a rise in permeability of blood vessels and is thought to play an important role in pain generation, inflammation and blood flow adjustment. Accordingly, pharmaceuticals having an inhibiting action for liberation of bradykinin have been shown to express various pharmaceutical effects such as analgesic, anti-inflammatory and anti-edema actions.

It has been clarified that the present extract has a suppressive action for liberation of bradykinin (*Eur. J. Pharmacol.*, vol. 157, no. 1, pages 93-99, 1988) and the pharmacological action as such is shown to be based on an inhibitory action for the production of a kallikrein-like substance. A method quantitatively to measure an inhibitory ability of a drug for the production of a kallikrein-like substance has been developed (*Kiso to Rinsho*, vol. 20, no. 17, pages 8889-8895, 1986).

The present invention relates to a dried product obtained in an intermediate step for the manufacture of the final product having a KPI activity stipulated in approved "Specification and Testing Methods" of oral preparations containing an extract from inflammatory rabbit skin inoculated with vaccinia virus as an effective ingredient. The present invention also relates to a process for the manufacture of said dried product. In respect of the dried product of the present extract, for example in Japanese Patent Laid-Open No. Sho-53/101, 515 or the like, there is only description that it is evaporated to dryness in vacuo. And, there has been no prior art where a specific process for the manufacture of a dried product having a KPI activity in the manufacture of oral preparations from the present extract is disclosed.

In making the present extract into pharmaceutical preparations as solid preparations for oral administration such as tablets, it is necessary to dry said extract. However, in a dried product of the present extract prepared by commonly-used concentration, drying, etc., no KPI activity is noted and, therefore, it has not been possible to manufacture solid preparations such as tablets having a KPI activity as the final preparation.

One of the difficulties encountered for many years by Nippon Zoki Pharmaceutical Co., the assignee of the present application, in making oral preparations from Neurotropin injections manufactured and sold by the company was to prepare a final preparation having a KPI activity. Although it has been empirically found that the final product manufactured by a certain process of Nippon Zoki Pharmaceutical Company has a KPI activity and development of Neurotropin tablets has been achieved, the assignee has retained it as know-how. The present inventors have systematically conducted studies for a drying method of the present extract for preparing a dried product having a KPI activity. As a result, it has been found that, when a saccharide, sugar alcohol or ascorbic acid is added to and mixed with the present extract before said extract reaches dryness and then it is dried, a dried product of the present extract having a KPI activity is obtained and the optimum pH, etc. have been also been found whereupon the present invention has been achieved.

The present invention provides a dried product of an extract from inflammatory rabbit skin inoculated with vaccinia virus having an inhibitory activity for the production of a kallikrein-like substance and, in final form, said dried product is able to be used as a material for the manufacture of solid preparations such as tablets, granules, diluted powder and fine particles having a KPI activity.

SUMMARY OF THE INVENTION

The present invention relates to a dried product of an extract from inflammatory rabbit skin inoculated with vaccinia virus having an inhibitory activity for the production of a kallikrein-like substance and also to a process for the manufacture of said dried product. To be more specific, it relates to a process for the manufacture of dried product of the present extract which is characterized in that, in drying the present extract, a saccharide, sugar alcohol or ascorbic acid is added thereto and mixed therewith before said extract reaches dryness and then the mixture is dried. In accordance with said process for the manufacture, a dried product of the present extract having a KPI activity is able to be prepared and it is now possible to manufacture solid preparations such as tablets finally having a KPI activity.

DETAILED DESCRIPTION OF THE INVENTION

Although the present extract such as an extract from inflammatory rabbit skin inoculated with vaccinia virus is able to be manufactured by the method which will be mentioned later, a characteristic feature of the process of the present invention is that, in drying the present extract, a saccharide, sugar alcohol or ascorbic acid is added thereto and mixed therewith before said extract reaches dryness and then the mixture is dried. Examples of the saccharide are a monosaccharide such as glucose, mannose, arabinose, xylose, galactose and sorbose, an oligosaccharide such as lactose, sucrose, maltose, raffinose and melezitose and a polysaccharide such as pullulan, dextrin, β-dextrin and dextran. As the sugar alcohol, mannitol, maltitol, lactitol, palatinit and sorbitol can be used in the present invention. With regard to the saccharide, sugar alcohol and ascorbic acid to be added, one of the above-mentioned ones may be used or two or more thereof may be used in combination. With regard to the polysaccharide, that which is insoluble in water is not suitable for the present invention and a polysaccharide which is soluble in water is able to be used in the present invention. As used herein, the polysaccharide which is insoluble in water corresponds to "rarely soluble" in Rule 23 of the Japanese Pharmacopoeia (Fourteenth Revision) and its examples are crystalline cellulose and starch.

The pharmaceutically effective amount of the saccharide, sugar alcohol or ascorbic acid which may be employed depends upon the kind of the saccharide or sugar alcohol used, concentration of the extract, etc. When lactose, is used in an extract to be tested mentioned in the following Example 1, not less than 0.1% by weight is preferred and, in order to prepare a dried product of the present extract having a high KPI activity with a good reproducibility, it is more preferred to add not less than 0.5% by weight of the additive.

With regard to a drying means, concentration and drying which are commonly used in preparing pharmaceutical preparations may be utilized. For example, as to a means for concentrating under a mild condition, vacuum drying in which heating at too high temperature is not conducted but water is removed by evaporating in vacuo under warm dipping (35° C. to 45° C.) may be exemplified. In embodiments of the invention an excipient containing the above-mentioned saccharide, sugar alcohol or ascorbic acid and the like may be added to the present extract or to a concentrate thereof, kneaded and granulated, and then dried to give a granular dried product of the present invention. In concentrating the present extract, it is preferred to conduct it at a pH of the solution which is 10 or lower and, in order to prepare a dried product of the present extract having a high KPI activity, it is more preferred to conduct it by adjusting the pH to 8.5 to 9.7.

As to addition of the saccharide, sugar alcohol or ascorbic acid in the present invention, it may be added to the present extract in its initial stage or may be added after concentrating to some extent. However, when it is added after the extract reaches dryness as in the case of common methods for the manufacture of solid preparations, no KPI activity is achieved in the finally manufactured dried product. In the manufacture of a solid preparation such as tablets according to the present invention, the preparation may be manufactured using various additives and methods as shown in General Rules for Pharmaceutical Preparations in the Japanese Pharmacopoeia (Fourteenth Revision). For example, a dried product of the present extract prepared by concentration and drying after addition of the above saccharide, sugar alcohol or ascorbic acid may be made into granules by an appropriate means either directly or after uniformly mixing with appropriate additives such as an excipient, binder, disintegrating agent or others and then subjected to a compression molding after addition of a lubricant or the like, and a method where the uniform mixture is directly subjected to a compression molding. It is also possible to make the present extract into tablets by a method where, when the present extract is concentrated to some extent, the above saccharide, sugar alcohol or ascorbic acid and other additives such as excipient, binder and disintegrating agent are added, homogeneously mixed, kneaded and subjected to granulation and drying by an appropriate means and the resulting dried product is subjected to a compression molding after addition of a lubricant or the like. If necessary, coloring agent, corrigent, etc. may be added and it is also possible to make or apply a coating using an appropriate coating agent.

The present extract used for the manufacture of the dried product of the present invention may be prepared in such manner that inflammatory rabbit skin tissues inoculated with vaccinia virus are crushed, an extracting medium is added thereto, tissue pieces are removed, a treatment for removal of protein (deproteinization) is conducted, the resulting product is adsorbed with an adsorbent and the effective ingredient is eluted therefrom.

As used herein, rabbit covers all animals belonging to Lagomorpha. Thus, the rabbit may be any of, for example, *Oryctolagus cuniculus*, hare (Japanese hare), mouse hare and snowshoe rabbit and, in Japan, it is easy to use family rabbit (in Japanese "Kato") which has been bred since old time and frequently used as a domestic animal or an experimental animal.

The present extract is, for example, manufactured by the following procedures:

(a) Inflammatory skin tissues of rabbit inoculated with vaccinia virus are collected, and the finely cut inflammatory tissues are crushed. An extracting medium such as water, phenol water, saline or phenol-added glycerin water is added, and then an extracted fluid (filtrate or supernatant) is obtained by filtration or centrifugation.

(b) The pH of the above extracted fluid is made acidic and it is heated for deproteinization. The deproteinized solution is subsequently made alkaline and heated, after which it undergoes filtration or centrifugation.

(c) The obtained filtrate or supernatant is made acidic, then adsorbed by an adsorbent such as activated carbon or kaolin.

(d) An extracting solvent such as water is added to the above adsorbent, the pH is made alkaline and the adsorbed component is eluted, thereby obtaining an extract from inflammatory tissue inoculated with vaccinia virus. Thereafter, the eluate can be suitably adjusted to natural pH to make a material for drug preparation.

Each step mentioned above is described in detail as follows:

Step (a):

Inflammatory skin tissues of rabbit inoculated with vaccinia virus are collected, ground and made into an emulsified suspension by adding 1 to 5 times as much extracting solvent thereto. Examples of the extracting solvent applicable are distilled water, physiologically saline solution, weakly acidic to weakly basic buffers, etc. If necessary, stabilizers such as glycerol, antibacterial/antiseptic agents such as phenol, inorganic salts such as sodium chloride, potassium chloride, magnesium chloride, etc. may be added thereto. At that time, the extraction can be made easier by subjecting the admixture to a treatment by means of freezing/melting, ultrasonic wave, cell membrane dissolving enzymes or surface-active agents.

Step (b):

The resulting milky extract is filtered or centrifuged to remove the tissue residue and then proteins are removed therefrom. Removal of the proteins can be carried out by known methods, for example, treatments by means of heating, ultrasonic wave, protein denaturating agents such as acids, bases, urea, guanidine, organic solvents, surface-active agents, etc., isoelectric precipitation, salting-out, can be employed. Then the insoluble proteins precipitated therefrom are removed by means of filtration using filter paper (cellulose, nitrocellulose, etc.), glass filter, Celite, Seitz filter, etc. as well as ultrafiltration, gel filtration, ion exchange resin, centrifugation and the like.

Step (c):

The resulting extract containing effective components is adjusted to acidic, preferably to pH 3.5-5.5, by an acid such as hydrochloric acid, sulfuric acid or hydrobromic acid, and adsorbed with an adsorbent. Examples of the applicable adsorbent are activated charcoal, kaolin, etc. The adsorbent is added to the extract followed by stirring or the extract is passed through a column filled with the adsorbent whereby the effective component can be adsorbed.

Step (d):

In eluting the effective component from the adsorbent, an extracting solvent is added to the adsorbent, and the elution is carried out at room temperature or by heating to some extent or with stirring, and then the adsobent is removed by conventional means such as filtration whereby the elution can be achieved. The extracting solvent applicable is a basic solvent, for example, water, methanol, ethanol, isopropanol or a mixed solution thereof which is adjusted to basic pH, preferably, water adjusted to pH 9-12 can be utilized.

The extract (eluted solution) obtained as above can be prepared to a preferred formulation suitable for drug material and medical preparations. For example, the solution is prepared to drug material by adjusting to approximately neutral or appropriate pH.

EXAMPLES

The examples of the method for manufacturing the present extract are as follows:

Referential Example 1

Skins of healthy adult rabbits were inoculated with vaccinia virus to cause inflammation. The inflammatory skins were removed, finely cut and phenol water was added thereto. The mixture was filtered with pressure, and the resulting filtrate was adjusted to pH 5 with hydrochloric acid and then heated at 90-100° C. for 30 minutes. Proteins were removed by filtration, the filtrate was adjusted to pH 9 with sodium hydroxide, further heated at 90-100° C. for 15 minutes and filtered. The filtrate was adjusted to about pH 4, stirred for 2 hours after adding 2% of activated charcoal, and centrifuged. The resulting activated charcoal was mixed with water, adjusted to pH 10 with sodium hydroxide, stirred at 60° C. for 1.5 hours and centrifuged to give a supernatant. The activated charcoals precipitated by centrifugation were mixed with water, adjusted to pH 11 with sodium hydroxide, stirred at 60° C. for 1.5 hours and centrifuged to give a supernatant. Both of the supernatants obtained were combined and neutralized with hydrochloric acid to give an extract from inflammatory tissue inoculated with vaccinia virus. In the following pharmacological studies, the extract was adjusted to appropriate concentrations to be used.

Referential Example 2

Skins of healthy adult rabbits were inoculated with vaccinia virus to cause inflammation. The inflammatory skins were aseptically removed, finely cut and phenol-added glycerin water was added thereto. The mixture was ground using a homogenizer to prepare an emulsion. The emulsion was filtered with centrifugation, and the resulting filtrate was adjusted to pH 4.8-5.5 with hydrochloric acid, heated at 100° C. with a steam flow and then filtered. The filtrate was further filtered with a Seitz filter, adjusted to pH 9.2 with sodium hydroxide, heated at 100° C. and filtered. The filtrate was adjusted to pH 4.5, stirred for 1-5 hours after adding 1.5% of activated charcoal, and filtered. The activated charcoal was mixed with water, adjusted to pH 9.4-10 with sodium hydroxide, stirred for 3-5 hours and filtered. The resulting filtrate was neutralized with hydrochloric acid and dried in vacuo.

Referential Example 3

Skins of healthy adult rabbits were inoculated with vaccinia virus to activate or stress the tissues. The activated skins were aseptically removed, finely cut and water was added thereto. The mixture was ground using a homogenizer to prepare an emulsion. The emulsion was filtered with pressure, and the resulting filtrate was adjusted to pH 5.0 with hydrochloric acid and heated at 100° C. with a steam flow. Proteins were removed by filtration, the filtrate was adjusted to pH 9.1 with sodium hydroxide, heated at 100° C. and filtered. The filtrate was adjusted to pH 4.1, stirred after adding 2% of activated charcoal, and the mixture was filtered to obtain a filtrate and a first batch of recovered activated charcoal. To the filtrate was added 5.5% of activated charcoal and the mixture was stirred for 2 hours, and filtered to obtain a second batch of recovered activated charcoal. The first batch of recovered activated charcoal was mixed with water, adjusted to pH 9.9 with sodium hydroxide, stirred at 60° C. for 1.5 hours and filtered. Water was then added to the first batch of the activated charcoal and to the second batch of activated charcoal. The pH of each batch was then adjusted to pH 10.9 with sodium hydroxide, and each batch was stirred at 60° C. for 1.5 hours and then filtered. The resulting filtrates were combined, neutralized with hydrochloric acid, desalted using electrodialysis with a membrane (molecular weight: 100), and dried in vacuo.

Method for Measuring the KPI Activity The inhibitory action for production of plasma kallikrein-like substances (KPI activity) of the tested drug was measured according to the method described in the literature (*Kiso to Rinsho*, vol. 20, no. 17, pages 8889-8895, 1986). Namely, as described in detail at page 8890 of the literature, the solution of the tested drug was mixed with normal human plasma diluted with saline. A suspension of kaolin was added to the mixture to initiate the reaction producing plasma kallikrein. After a constant time, a specific inhibitor of blood coagulation factor XII such as lima bean trypsin inhibitor (LBTI) was added to terminate the reaction producing kallikrein, and then the produced kallikrein was quantitatively determined by using a coloring synthetic substrate (S-2302, Chromogenix). Since the synthetic substrate S-2302 releases coloring p-nitroaniline by kallikrein action, the amount (activity) of produced kallikrein can be determined by measuring the amount of liberated p-nitroaniline by the measurement of absorbance at 405 nm. The KPI activity of the tested drug can be evaluated by determining the difference in absorbance between a control group (a group without the tested drug) and the group to which the tested drug is added.

It is able to be appropriately set judging criteria whether the KPI activity is available and, in Neurotropin preparations, difference in absorbencies is stipulated to be not less than 0.1 and said stipulation is used in the dried product of the present invention as well.

Example 1

An extract for the test was prepared in such a manner that the weight of dried product of an extract from inflammatory rabbit skin inoculated with vaccinia virus manufactured according to the above-mentioned Referential Example 1 was made to be 1 mg/mL where the pH was 9.5. One hundred mL of said extract for the test was taken, concentrated and dried in vacuo under warm dipping of about 40° C. Water was added to the dried product to dissolve it whereupon a test solution of 1 mg/mL was prepared. The test solution (0.2 mL) and 0.2 mL of 0.5M sodium chloride solution were mixed and, after that, a measuring test was conducted according to the test operation in the above-mentioned method for measuring the KPI activity. Table 1 shows examples of test results (n=2) in the case where the extract for the test was directly concentrated and dried and in the case where the extract for the test prepared by addition of lactose so as to make 1% by weight was then concentrated and dried. Water was used as a control in this test and in the following tests as well.

TABLE 1

| Test solution | Absorbance Observed value | Absorbance Mean value | Difference in absorbances KPI activity |
|---|---|---|---|
| Control | 0.361 0.361 | 0.361 | |
| Non-addition of lactose | 0.352 0.373 | 0.363 | 0.002 |
| Addition of lactose | 0.073 0.065 | 0.069 | 0.292 |

The above-mentioned test system is a system where the amount of p-nitroaniline liberated from a coloring synthesis substrate by enzymatic activity of the produced kallikrein was measured by means of absorbance. In the control, a certain amount of kallikrein was produced and the absorbances as mentioned in the upper row of Table 1 were measured. While, when a test substance inhibiting the kallikrein product was present in the reaction system, the measured absorbances showed low values as a result of lowering of the kallikrein production. Thus, it shows that, when the difference in absorbances from the control is high, the KPI activity of the test substance is high. As shown in Table 1, the absorbance of the test solution which was concentrated and dried without addition of lactose (Non-addition of lactose) was the same as that of the control whereby no KPI activity was noted at all. On the contrary, in a test solution concentrated and dried after addition of lactose (Addition of lactose), an apparent KPI activity was measured whereby it is shown that a dried product of the present extract having a KPI activity is able to be manufactured by addition of lactose.

Example 2

The same as in Example 1, a comparison was performed between the case where concentration and drying were conducted after addition of lactose to the extract to be tested and the case where lactose was added after concentration and drying of the extract to be tested. Measurement was also conducted for a lactose solution as a blank. Examples of the results are shown in Table 2. As shown by the results in Table 2, only a test solution where lactose was added before concentrating and drying showed a KPI activity and, in the case where lactose was added after concentration and drying of the extract to be tested and in the case of a solution containing lactose only, no KPI activity was noted at all.

TABLE 2

| Test solution | Absorbance Observed value | Absorbance Mean value | Difference in absorbances KPI activity |
|---|---|---|---|
| Control | 0.356 0.371 | 0.364 | |
| Addition of lactose | 0.066 0.059 | 0.063 | 0.301 |
| Addition of lactose after drying | 0.341 0.342 | 0.342 | 0.022 |
| Lactose solution (1 wt %) | 0.365 0.384 | 0.375 | 0.011 |

Example 3

The result where additives other than lactose were added to an extract to be tested before concentrating and drying in the same manner as in Example 1 is shown in Table 3-1 below. The cases where a saccharide such as glucose (monosaccharide) and pullulan (polysaccharide) is added (1% by weight in each of the cases) before drying showed a KPI activity but the cases where an excipient other than a saccharide such as calcium hydrogen phosphate or a water-insoluble polysaccharide such as crystalline cellulose or corn starch was used showed no KPI activity.

TABLE 3-1

| Test solution | Absorbance Observed value | Absorbance Mean value | Difference in absorbances KPI activity |
|---|---|---|---|
| Control | 0.330 0.315 | 0.323 | |

TABLE 3-1-continued

| Test solution | Absorbance Observed value | Absorbance Mean value | Difference in absorbances KPI activity |
|---|---|---|---|
| Addition of glucose | 0.075<br>0.063 | 0.069 | 0.254 |
| Addition of calcium hydrogen phosphate | 0.283<br>0.294 | 0.289 | 0.034 |
| Control | 0.322<br>0.327 | 0.325 | |
| Addition of pullulan | 0.095<br>0.093 | 0.094 | 0.231 |
| Addition of crystalline cellulose | 0.273<br>0.280 | 0.277 | 0.048 |
| Control | 0.330<br>0.317 | 0.324 | |
| Addition of corn starch | 0.280<br>0.326 | 0.303 | 0.021 |

In the same manner, mannitol, maltitol, lactitol, palatinit (monohydrate), sorbitol and ascorbic acid were used (the same amount is also added) and the results are shown in Table 3-2. In the tested solution of the dried product where the mannitol, maltitol, sorbitol, lactitol, palatinit or ascorbic acid was added to the extract and it was concentrated and dried, the KPI activity was clearly observed. Therefore, the dried product of the present extract having KPI activity can be manufactured by addition of ascorbic acid or a sugar alcohol constituted of at least one hexose.

TABLE 3-2

| Test solution | Absorbance Observed value | Absorbance Mean value | Difference in absorbance KPI activity |
|---|---|---|---|
| Control | 0.368<br>0.370 | 0.369 | |
| Addition of sorbitol | 0.207<br>0.239 | 0.223 | 0.146 |
| Control | 0.346<br>0.359 | 0.353 | |
| Addition of mannitol | 0.095<br>0.084 | 0.090 | 0.263 |
| Addition of ascorbic acid | 0.039<br>0.038 | 0.039 | 0.314 |
| Control | 0.351<br>0.352 | 0.352 | |
| Addition of lactitol | 0.042<br>0.040 | 0.041 | 0.311 |
| Addition of palatinit | 0.114<br>0.116 | 0.115 | 0.237 |
| Control | 0.336<br>0.350 | 0.343 | |
| Addition of maltitol | 0.044<br>0.041 | 0.043 | 0.300 |

Example 4

Results of the cases where the same operation as in Example 1 was conducted using a saccharide other than the saccharides mentioned in the above Examples is shown in Table 4 (1% by weight of a saccharide was added to the extract to be tested in each of the cases). Results of the cases where 0.5% by weight or 0.1% by weight of lactose was added is also shown in the same table. Table 4 summarizes the results of plural tests (absorbance value of the control: 0.306 to 0.363) and absorbances of the test solutions and difference (KPI activity) between those and the control are shown.

TABLE 4

| Additive to the test solution | Absorbance Mean value of 2 observed values | Difference in absorbance from the control KPI activity |
|---|---|---|
| Arabinose | 0.056 | 0.268 |
| Xylose | 0.053 | 0.271 |
| Mannose | 0.049 | 0.275 |
| Galactose | 0.072 | 0.252 |
| Sorbose | 0.056 | 0.250 |
| Sucrose | 0.107 | 0.249 |
| Maltose | 0.060 | 0.290 |
| Raffinose | 0.084 | 0.264 |
| Melezitose | 0.097 | 0.251 |
| Dextrin | 0.104 | 0.242 |
| β-Cyclodextrin | 0.240 | 0.121 |
| Dextran | 0.186 | 0.177 |
| Lactose 0.5 wt | 0.047 | 0.273 |
| Lactose 0.1 wt | 0.143 | 0.177 |

Example 5

Weight of the product of the present extract after being evaporated to dryness was measured the same as in Example 1 and an extract to be tested was prepared so as to obtain a concentration of 1 mg/mL and a pH of 8.8 to 9.3. Ten mL of said extract to be tested was taken and concentrated in vacuo and temperature control was performed so that the temperature of the concentrate was maintained at about 40° C. Concentration was conducted until 200 mL (50 mg/mL), 200 g of lactose and about 160 g of other excipient, disintegrating agent, etc. were added thereto and kneaded therewith and the mixture was granulated and dried. The resulting dried granules prepared as such were able to be formulated into a solid preparation for oral use. For example, magnesium stearate or another lubricant was added thereto followed by subjecting the admixture to compressive molding to manufacture tablets.

The above-mentioned granules in an amount calculated to contain 50 mg of the dried product of the present extract were taken and 50 mL of a Tris hydrochloride buffer (pH 8.0) was added thereto and stirred therewith. After that, the mixture was filtered using a membrane filter, the filtrate was used as a test solution and its KPI activity was measured the same as in Example 1. Also, in the above operation before addition of an excipient such as lactose, a 50 mg/mL concentrated solution of the present extract was taken and diluted with water to 1 mg/mL and measured as well. Examples of the results are shown in Table 5. As shown in Table 5, any of the concentrated solution of the present extract and the dried granules prepared by adding an excipient such as lactose to said concentrate followed by kneading granulating and drying showed a KPI activity.

TABLE 5

| Test solution | Absorbance Observed value | Absorbance Mean value | Difference in absorbance KPI activity |
|---|---|---|---|
| Control | 0.332<br>0.335 | 0.334 | |
| Dried granules solution | 0.054<br>0.054 | 0.054 | 0.280 |
| Concentrated solution | 0.048<br>0.046 | 0.047 | 0.287 |

Example 6

Table 0.6 shows examples of the results where the extract to be tested was adjusted to various pH values in concentrating and drying the extract to be tested. When the pH was 10.5, a KPI activity was hardly noted and, as the pH was changed from 9.5 to acidic, a KPI activity of the dried product gradually lowered.

TABLE 6

| Test solution | Absorbance | | Difference in absorbance KPI activity |
|---|---|---|---|
| | Observed value | Mean value | |
| Control | 0.338 | 0.335 | |
| | 0.332 | | |
| Concentrated solution (pH 6.0) | 0.178 | 0.174 | 0.161 |
| | 0.169 | | |
| Concentrated solution (pH 8.5) | 0.133 | 0.128 | 0.207 |
| | 0.122 | | |
| Concentrated solution (pH 9.5) | 0.053 | 0.050 | 0.285 |
| | 0.047 | | |
| Concentrated solution (pH 10.0) | 0.241 | 0.232 | 0.103 |
| | 0.223 | | |
| Concentrated solution (pH 10.5) | 0.272 | 0.272 | 0.063 |
| | 0.272 | | |

Formulation Example 1

According to the same method as mentioned in Example 5, dried granules of the present extract were manufactured and subjected to a compressive molding to manufacture tablets. Thus, the components were kneaded so that each tablet contained 4 mg of dried product of an extract from inflammatory rabbit skin inoculated with vaccinia virus, 104 mg of lactose, 40 mg of crystalline cellulose and 20 mg of carboxymethyl cellulose and then subjected to granulation and drying. Magnesium stearate (content in a tablet: 2 mg) was added to and mixed with the dried granules followed by subjecting the admixture to compressive molding using a tabletting machine to manufacture tablets.

Formulation Example 2

According to the same manner as in Formulation Example 1, tablets were manufactured where each tablet contained 5 mg of dried product of an extract from inflammatory rabbit skin inoculated with vaccinia virus, 80 mg of lactose, 20 mg of calcium hydrogen phosphate, 42 mg of lowly-substituted hydroxypropyl cellulose, 2 mg of hydroxypropyl cellulose and 1 mg of magnesium stearate. The resulting crude tablets were subjected to a spray coating with a coating solution (prepared by mixing 40 g of hydroxypropyl cellulose, 10 g of Macrogol 6000, 3 g of titanium oxide, 5 g of talc, 0.5 kg of lake dye and 941.5 g of pure water) to manufacture film-coated tablets. KPI activity of the above dried granules and tablet were measured, and both the dried granules and tablet had KPI activity. Furthermore, when they were formulated by using D-mannitol instead of lactose, the same results were noted.

Besides the above, the dried product of the present invention is appropriately able to be processed into solid preparations for oral administration such as diluted powder, granules or capsules.

The present invention provides a dried product having an inhibitory activity for the production of a kallikrein-like substance of an extract from inflammatory rabbit skin inoculated with vaccinia virus. The dried product can be utilized for the manufacture of pharmaceutical preparations such as solid preparations including tablets. A process for the manufacture of the dried product of the present extract having a KPI activity is essentially important in the manufacture of solid preparations for oral administration where the present extract is an effective ingredient. The present invention is epoch-making whereby it is now possible to provide solid preparations for oral administration having a KPI activity and containing the present extract as a pharmaceutically effective ingredient. The solid preparations containing a pharmaceutically effective amount of the extract may be administered orally to patients in need of treatment for conditions responsive to an inhibiting action for liberation of bradykinin to provide various pharmaceutical effects such as analgesic, anti-inflammatory and anti-edema actions. At the same time, the present invention can be carried out by a simple operation, that is, before getting the present extract to dryness, a saccharide, sugar alcohol or ascorbic acid is added thereto and mixed therewith under a predetermined condition followed by drying. As such, it is a very useful process in view of economy where no specific additive or the like is necessary.

What is claimed is:

1. A process for the manufacture of a dried product having an inhibitory activity for the production of a kallikrein from a liquid extract from inflammatory rabbit skin inoculated with vaccinia virus comprising admixing said extract with at least one member selected from the group consisting of glucose, mannose, arabinose, xylose, galactose, sorbose, lactose, sucrose, maltose, raffinose, melezitose, pullulan, dextrin, β-cyclodextrin, dextran, mannitol, maltitol, lactitol, palatinit, sorbitol, and ascorbic acid to obtain a mixture, and then drying the mixture to obtain a dried product having an inhibitory activity for the production of a kallikrein, wherein drying of said extract is carried out at a pH of 8.8 to 9.7.

2. The process as claimed in claim 1 wherein said at least one member is added to and mixed with an extract from inflammatory rabbit skin inoculated with vaccinia virus and then the mixture is concentrated and dried.

3. The process as claimed in claim 2 wherein the concentration of the extract is carried out at a pH of 8.8 to 9.7.

4. The process as claimed in claim 1 wherein an extract from inflammatory rabbit skin inoculated with vaccinia virus is concentrated and, before the concentrated extract reaches dryness, said at least one member is added to and mixed with the concentrated liquid extract and then the mixture is dried.

5. The process as claimed in claim 1 wherein said at least one member is selected from the group consisting of glucose, mannose, arabinose, xylose, galactose, sorbose, lactose, sucrose, maltose, raffinose, melezitose, pullulan, dextrin, β-cyclodextrin and dextran.

6. The process as claimed in claim 1 wherein said at least one member is selected from the group consisting of mannitol, maltitol, lactitol, palatinit and sorbitol.

7. The process as claimed in claim 1 wherein the amount of said at least one member is at least 0.1% by weight, based upon the weight of the extract and said at least one member.

8. The process as claimed in claim 1 wherein said drying comprises vacuum drying.

9. The process as claimed in claim 1 wherein said mixture is granulated and dried to obtain granules.

10. The process as claimed in claim 9 wherein said granules are formed into tablets.

11. The process as claimed in claim 10 wherein said tablets are spray coated with a coating solution.

12. The process as claimed in claim 1 wherein the drying of the extract is carried out at a pH of 8.8 to 9.5.

13. The process as claimed in claim 1 wherein the drying of the extract is carried out at a pH of 8.8 to 9.3.

14. A process for the manufacture of a dried product having an inhibitory activity for the production of a kallikrein, which method comprises the steps of:
   (i) providing a liquid extract from inflammatory rabbit skin inoculated with vaccinia virus,
   (ii) adding thereto and mixing therewith, before the extract reaches dryness, at least one member selected from the group consisting of glucose, mannose, arabinose, xylose, galactose, sorbose, lactose, sucrose, maltose, raffinose, melezitose, pullulan, dextrin, β-cyclodextrin, dextran, mannitol, maltitol, lactitol, palatinit, sorbitol, and ascorbic acid to obtain a mixture, and then
   (iii) drying the mixture to obtain a dried product having an inhibitory activity for the production of a kallikrein, wherein drying of said extract is carried out at a pH of 8.8 to 9.7.

15. The process as claimed in claim 14 wherein after step (ii) the obtained mixture is concentrated and dried.

16. The process as claimed in claim 15 wherein the concentration of the extract is carried out at a pH of 8.8 to 9.7.

17. The process as claimed in claim 14 wherein the extract is concentrated prior to step (ii).

* * * * *